US012729390B2

(12) United States Patent
Huang et al.

(10) Patent No.: US 12,729,390 B2
(45) Date of Patent: Sep. 8, 2026

(54) FERMENTATION PROCESS FOR PREPARING POSTBIOTIC WITH BY-PRODUCT OF WHEAT PROCESSING

(71) Applicant: XUCHANG UNIVERSITY, Xuchang (CN)

(72) Inventors: Jihong Huang, Luoyang (CN); Yinchen Hou, Luoyang (CN); Aimei Liao, Luoyang (CN); Jingbo Zhou, Luoyang (CN); Weiyun Guo, Luoyang (CN); Ling Fan, Luoyang (CN); Guanghai Yu, Luoyang (CN); Penghua Shu, Luoyang (CN); Long Pan, Luoyang (CN)

(73) Assignee: XUCHANG UNIVERSITY, Xuchang (CN)

( * ) Notice: Subject to any disclaimer, the term of this patent is extended or adjusted under 35 U.S.C. 154(b) by 448 days.

(21) Appl. No.: 18/284,867

(22) PCT Filed: Nov. 12, 2021

(86) PCT No.: PCT/CN2021/130222
§ 371 (c)(1),
(2) Date: Sep. 29, 2023

(87) PCT Pub. No.: WO2023/029213
PCT Pub. Date: Mar. 9, 2023

(65) Prior Publication Data

US 2024/0182937 A1 Jun. 6, 2024

(30) Foreign Application Priority Data

Sep. 3, 2021 (CN) ........................ 202111031651.3

(51) Int. Cl.

| | |
|---|---|
| ***C12N 1/20*** | (2026.01) |
| ***C12P 7/6409*** | (2022.01) |
| ***C12P 19/04*** | (2006.01) |
| *C12R 1/12* | (2006.01) |
| *C12R 1/20* | (2006.01) |

(52) U.S. Cl.
CPC ............ *C12P 19/04* (2013.01); *C12P 7/6409* (2013.01); *C12R 2001/12* (2021.05); *C12R 2001/20* (2021.05)

(58) Field of Classification Search
CPC .... C12P 19/04; C12P 7/6409; C12R 2001/12; C12R 2001/20; C12R 2001/01; C12N 1/20; C12N 1/205; Y02P 60/87; A23L 33/00; A23L 29/065; A23V 2002/00
See application file for complete search history.

(56) References Cited

FOREIGN PATENT DOCUMENTS

| | | | |
|---|---|---|---|
| CN | 102249754 | A | 11/2011 |
| CN | 108753901 | A | 11/2018 |
| CN | 110143732 | A | 8/2019 |
| CN | 110643654 | A | 1/2020 |
| CN | 113875975 | A | 1/2022 |
| WO | 2020198463 | A1 | 10/2020 |
| WO | 2021074649 | A2 | 4/2021 |

OTHER PUBLICATIONS

Lu Juan, et al., Screening and identification of an exopolysaccharide—producing strain and the investigation of its polysaccharide, Nat Prod Res Dev, 2020, pp. 1484-1490, 1528, vol. 32, English Abstract Only.

*Primary Examiner* — Sharmila G Landau
*Assistant Examiner* — Ashley T White
(74) *Attorney, Agent, or Firm* — Bayramoglu Law Offices LLC

(57) ABSTRACT

A fermentation process for preparing a postbiotic with a by-product of wheat processing includes: preparation of a material; inoculation of *Paenibacillus polymyxa* (*P. polymyxa*)+*Brachybacterium paraconglomeratum* (*B. paraconglomeratum*)+*Flavobacterium pectinovorum* (*F. pectinovorum*) as fermentation strains; and isolation and extraction of the postbiotic. Since wheat starch wastewater and wheat bran include abundant nutrient components, the wheat starch wastewater and wheat bran can be used to prepare postbiotics, which is conducive to reducing a wastewater treatment cost of a related enterprise and protecting the environment, and can turn waste into treasure and increase an added value of an agricultural product. Preliminary experimental results show that, when no nutrients are additionally supplemented, marker products such as lipoteichoic acid (LTA) and short-chain fatty acids (SCFAs) in a prepared postbiotic solution are at high contents, which can extend an industrial chain of wheat deep-processing and improve an industrial value of deep processing technology.

5 Claims, 2 Drawing Sheets

FERMENTATION PROCESS FOR PREPARING POSTBIOTIC WITH BY-PRODUCT OF WHEAT PROCESSING

CROSS REFERENCE TO THE RELATED APPLICATIONS

This application is the national phase entry of International Application No. PCT/CN2021/130222, filed on Nov. 12, 2021, which is based upon and claims priority to Chinese Patent Application No. 202111031651.3, filed on Sep. 3, 2021, the entire contents of which are incorporated herein by reference.

TECHNICAL FIELD

The present application belongs to the technical field of agricultural product processing, and specifically relates to a fermentation process for preparing a postbiotic with a by-product of wheat processing.

BACKGROUND

Main by-products generated during processing of wheat to prepare a flour include liquid process water (also known as wheat starch wastewater) and solid wheat bran (seed capsules obtained after ground wheat is sieved) resulting from wheat starch processing. However, in the prior art, because these by-products have a low nutrient content and can not easily be recycled, insufficient attention has been paid to these processing by-products, and there are relatively-limited targeted technical development and technical reserves for these processing by-products.

In the technical field of food nutriology, postbiotic products are important nutritional products left after probiotic products are prepared. In general, postbiotics refer to metabolite components of probiotics generated after processing with the probiotics, and include bacteria and metabolites. A representative component of a postbiotic is lipoteichoic acid (LTA), which is a key to determining the tolerance of the postbiotic to acids, alkalis, and heat. LTA is a special component of the cell wall of a gram-positive (G+) bacterium, and on the cell surface, LTA crosses a peptidoglycan (PGN) layer and is covalently linked to an oligosaccharide moiety of a glycolipid (such as diglucosyldiacylglycerol) in a plasma membrane through terminal phosphoric acid of LTA. Studies have shown that LTA is related to physiological activities such as permeability of cell membranes, irritation of immune cells, and regulation of immunoreactive proteins, and thus postbiotics generated after processing can play an important role in improvement and enhancement of the immune activity of a body.

Postbiotics, also known as biogenics or cell-removed supernatants, refer to soluble factors secreted due to metabolic activities of live bacteria (probiotics) or released after death and lysis of bacteria; and postbiotics can produce beneficial effects for a host. Generally, the soluble factors include short-chain fatty acids (SCFAs) (which are also known as volatile fatty acids (VFAs), including acetic acid, propionic acid, butyric acid, or the like), enzymes, polypeptides, polysaccharides, or the like. SCFAs are the most common metabolites generated during fermentation by probiotics in the human body, and can supply part of the energy required by the host (human body) and play a role in regulation of metabolism, division, and differentiation of cells. Other studies have shown that SCFAs are also special nutritional factors of intestinal epithelia, and can maintain the integrity of intestinal epithelial cells and the secretory function of goblet cells, play a regulatory role for gastrointestinal tracts, reduce the impact of pH value, an oxidation-reduction potential (ORP), or the like on the construction and composition of an intestinal flora, and prevent the colonization of exogenous pathogenic bacteria. Thus, SCFAs can be used as one of the main indexes for determining a nutritional value of a postbiotic.

In short, the deep development of a technique to prepare a postbiotic product with a high nutritional value from a relevant waste or by-product generated during wheat processing is of very important technical significance for extending a wheat processing industrial chain and improving a technical value of deep processing.

SUMMARY

In view of the fact that liquid process water (also known as wheat starch wastewater) and solid wheat bran generated during wheat processing are still rich in nutrients, an objective of the present application is to provide a fermentation process to prepare postbiotics with these by-products of wheat processing as raw materials, thereby laying a specific technical basis for improvement of an added value of wheat processing.

The technical solution of the present application is described in detail below.

A fermentation process for preparing a postbiotic with a by-product of wheat processing is provided, specifically including the following steps:

(1) Preparation of a Material thoroughly mixing a process water and a wheat bran resulting from wheat starch processing in a mass ratio of (1-12):1 (preferably (8-10):1), sterilizing a resulting mixture at 121° C. for 20 min, and cooling a sterilized mixture to room temperature to obtain a fermentation matrix;

(2) Inoculation of Fermentation Strains preparing each of *Paenibacillus polymyxa* (*P. polymyxa*) (CGMCC 1.15984), *Brachybacterium paraconglomeratum* (*B. paraconglomeratum*) (CGMCC 1.838), and *Flavobacterium pectinovorum* (*F. pectinovorum*) (CGMCC 1.12362) into a seed culture in which a number of viable bacteria is not less than $1\times10^6$/mL, and thoroughly mixing resulting seed cultures according to a volume ratio of 1:1:1 to obtain a mixed fermentation broth;

under sterile conditions, inoculating the mixed fermentation broth into the fermentation matrix in step (1) according to a mass proportion of 1% to 25% (preferably 10%), and conducting fermentation at 25° ° C. to 37° C. for 48 h to 192 h; and (3) Isolation and Extraction of the Postbiotic (which Includes the Main Components of LTA and SCFA)

after the fermentation in step (2) is completed, filtering a resulting fermentation system, subjecting a resulting filtrate to primary centrifugation at 1,000 r/min for 30 min, and collecting a resulting supernatant; and subjecting the collected supernatant to secondary centrifugation at 5,000 r/min for 30 min, collecting a supernatant obtained after the secondary centrifugation to obtain a postbiotic solution, and storing the postbiotic solution at 4° C.

The Present Disclosure has the Following Beneficial Effects

In a broad sense, wheat starch wastewater is wastewater generated during a process of preparing a starch or a starch deep-processing product (such as a starch sugar, glucose, or a starch derivative) with an agricultural product such as wheat as a raw material, and belongs to high-concentration organic wastewater. The wheat starch wastewater is easy to cause environmental pollution if directly discharged, and thus the wheat starch wastewater needs to undergo an anaerobic treatment before being discharged during production, which is also one of the main reasons why food starch plants are classified as highly-polluting enterprises. However, actual wastewater composition test results show that such wheat starch wastewater includes high contents of nutrients such as starches, proteins, and pentosans, and thus how to further utilize such wheat starch wastewater and reduce a treatment cost of such wastewater is one of the urgent technical problems to be solved by production enterprises such as starch plants.

Traditionally, wheat bran produced during processing of wheat into a flour is primarily used as an ingredient in an animal feed, and is inexpensive. However, nutrient test results show that the wheat bran includes high contents of nutrients such as proteins, fats, carbohydrates, and crude fibers. Therefore, how to deeply process the wheat bran to increase an economic added value of the wheat bran is one of the key technical issues in the deep processing industry of wheat to increase a value of the wheat.

Based on the state of the art, in view of a postbiotic preparation process and the fact that the wheat starch wastewater and wheat bran each include abundant nutrients, the present application designs and provides a fermentation process for preparing a postbiotic with a by-product of wheat processing, which is conducive to reducing a wastewater treatment cost of a related enterprise and protecting the environment, and can turn waste into treasure and increase an added value of an agricultural product.

Preliminary experimental results show that, when no nutrients are additionally supplemented, marker products such as LTA and SCFAs in a prepared postbiotic solution are at high contents, which can lay a specific technical foundation for preparation of related health products, and can also lay a specified technical foundation for extending an industrial chain of wheat deep-processing and improving an industrial value of deep processing technology.

DETAILED DESCRIPTION OF THE EMBODIMENTS

Figure 1:
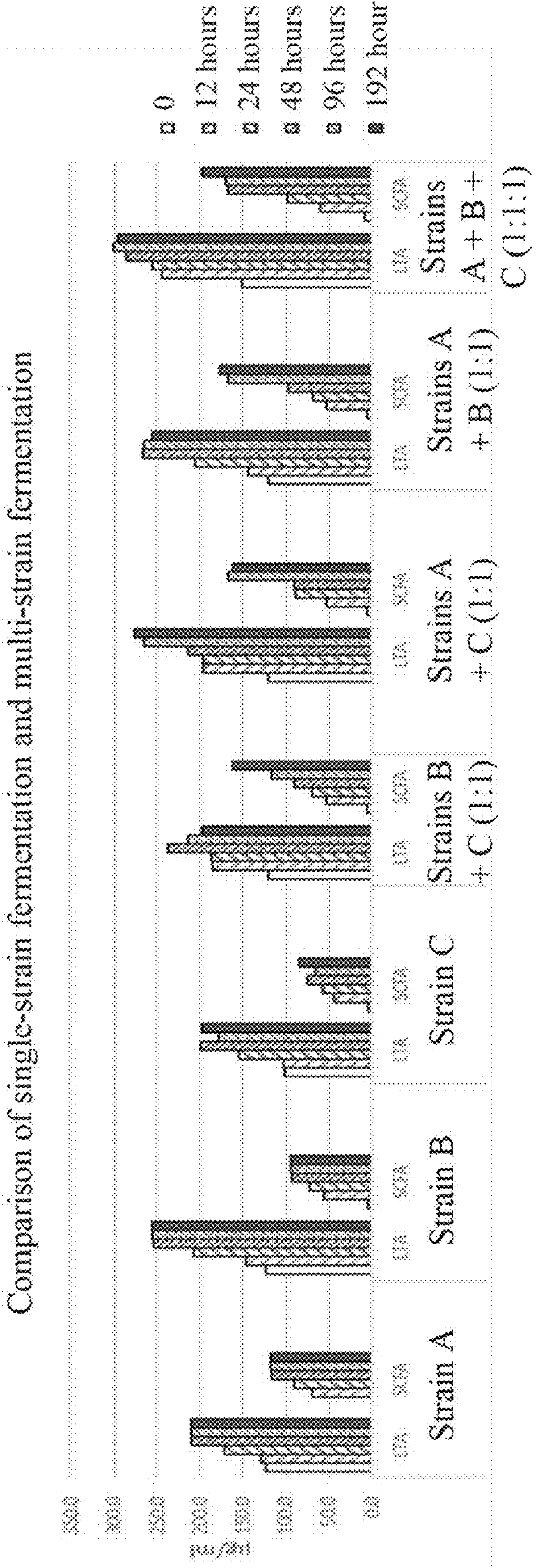
FIG. 1 shows an impact of different bacterial strain combinations on a fermentation effect.

The technical solutions of the present disclosure are further described below with reference to embodiments. Before specific embodiments are introduced, in order to facilitate those skilled in the art to understand the relevant research and development in the present disclosure in detail, some background experiments in the following embodiments are briefly described as follows.

Biological Materials:

Inoculated strains used during fermentation: *P. polymyxa* deposited in CGMCC on Nov. 30, 2016 with the accession No. CGMCC 1.15984, *B. paraconglomeratum* deposited in CGMCC with the accession No. CGMCC 1.838, and *F. pectinovorum* deposited in CGMCC on Oct. 15, 2012 with the accession No. CGMCC 1.12362, which are publicly-available strains and all are purchased directly from the China General Microbiological Culture Collection Center (CGMCC).

*P. polymyxa* refers to a group of rod-like bacteria with diversified physiological characteristics, which are spore-forming gram-positive bacteria; *P. polymyxa* lives in an aerobic or facultatively-anaerobic environment; *P. polymyxa* can decompose starches or polysaccharides, can produce acids, and can also produce active substances with functions of antagonizing microorganisms, promoting plant growth, or the like; and *P. polymyxa* may be Polymyxin, Colistin, Circulin, Jolipeptin, Polypeptins, Gatavalin, or Fusaricidins, for example.

*B. paraconglomeratum* refers to a group of club-shaped gram-positive bacteria, which can produce amylases.

*F. pectinovorum* can convert starches into organic acids (such as SCFAs) and other active ingredients during fermentation.

It should be explained and emphasized that the microbial strains that can produce amylases or starches in the prior art are not limited to the above three strains, but given the similar growth conditions of the above three strains (optimal growth temperature: 25° C. to 37° C., and optimal growth pH: about 7.0) and based on the convenience of unified control of growth conditions and the technical purpose of preparation of a postbiotic through fermentation in the present application, the above three strains are comprehensively selected for a specific fermentation experiment.

By-Products of Wheat Processing:

A process water sample and a wheat bran sample resulting from wheat starch processing are all from Henan Feitian Agricultural Development Co., Ltd.; and main nutrients and contents thereof in the samples are as follows:

TABLE 1

| Starch water composition (%, mass percentage) | | | | | | |
|---|---|---|---|---|---|---|
| Item | Total sugar, % | Crude protein, % | Crude fat, % | Starch, % | Crude fiber, % | Moisture content, % |
| Starch water | 1.6 | 0.7 | 0 | 0.1 | 0.6 | 97.0 |

TABLE 2

| Wheat bran composition (%, mass percentage) | | | | | | |
|---|---|---|---|---|---|---|
| Item | Total sugar | Crude protein | Crude fat | Starch | Crude fiber | Crude ash |
| Wheat bran (dry basis) | 39.63 | 18.66 | 2.28 | 27.6 | 6.92 | 4.91 |

EXAMPLES

With specific by-products of wheat processing as an example, the fermentation process for preparing a postbiotic with a by-product of wheat processing designed in the present application is specifically described by the inventors as follows:

(1) Preparation of a Material

The process water and wheat bran resulting from wheat starch processing were thoroughly mixed in a mass ratio of 5:1, sterilized at 121° C. for 20 min, and then cooled to room temperature to obtain a fermentation matrix.

(2) Inoculation of Fermentation Strains

Each of *P. polymyxa* (CGMCC 1.15984, strain A), *B. paraconglomeratum* (CGMCC 1.838, strain B), and *F. pectinovorum* (CGMCC 1.12362, strain C) was prepared into a seed culture in which a number of viable bacteria was $1\times10^6$, and resulting seed cultures were mixed according to a volume ratio of 1:1:1 to obtain a mixed fermentation broth in which a total number of viable bacteria was $1\times10^6$; and under sterile conditions, the mixed fermentation broth was inoculated into the fermentation matrix in step (1) according to a mass proportion of 10%, and fermentation was conducted at 28° C. for 192 h.

(3) Isolation and Extraction of the Postbiotic (Index Components: LTA and SCFA)

After the fermentation in step (2) was completed, a resulting fermentation system was filtered, a resulting filtrate was subjected to primary centrifugation at 1,000 r/min for 30 min, and a resulting supernatant was collected; and the collected supernatant was subjected to secondary centrifugation at 5,000 r/min for 30 min, a supernatant obtained after the secondary centrifugation was collected to obtain a postbiotic solution, and the postbiotic solution was stored at 4° C.

From the perspective of increasing a content of a postbiotic active ingredient, in order to determine an appropriate fermentation process, relevant fermentation process conditions were specifically explored by the inventors, and a specific process was briefly described as follows:

It should be noted that an LTA content was used as an evaluation index for an effect of the postbiotic (the LTA content was detected by an LTA ELISA kit of Shanghai Lanpai Biotechnology Co., Ltd. with reference to instructions of the kit), and SCFA was used as a marker component of the postbiotic to evaluate an effect of the postbiotic in the postbiotic solution (an SCFA content was detected by an SCFA ELISA kit of Shanghai Win-Win biochemical Co., Ltd. with reference to instructions of the kit).

(A) Impact of a Single Strain or a Mixed Strain on LTA and SCFA in a Fermentation Broth In order to investigate fermentation effects of single-strain fermentation and multi-strain fermentation, the strain A, the strain B, the strain C, and combinations of different strains (when different strains were used in combination, the different strains were in a volume ratio of 1:1 or 1:1:1; and before inoculation, a number of bacteria was $1\times10^6$, that is, a number of viable bacteria was $1\times10^6$ when a single strain was inoculated, and an initial total number of viable bacteria was also $1\times10^6$ when a combination of different strains was inoculated) each were inoculated for fermentation.

Fermentation was conducted at 28° ° C. for 192 h, and LTA and SCFA contents in a resulting fermentation broth were detected. Specific results were shown in FIG. 1.

It can be seen from FIG. 1 that, during either single-strain fermentation or multi-strain fermentation, the LTA and SCFA contents gradually increase with the extension of a fermentation time, but after a specified fermentation time, the LTA and SCFA contents are basically stable or even decrease, and thus a fermentation time of 45 h to 100 h can be adopted from the perspective of actual production efficiency; and from the perspective of an actual fermentation yield, the multi-strain fermentation leads to a better fermentation effect than the single-strain fermentation, where the fermentation with the strains A, B, and C has the optimal fermentation effect. Therefore, without increasing a production cost, it is most suitable to use a mixture of the three strains for fermentation. Therefore, subsequently, a mixture of the three strains is used for fermentation to prepare a postbiotic.

Specifically, in terms of a fermentation yield of a single strain, an SCFA yield of the strain A is 116.8, an SCFA yield of the strain B is 93.4, and an SCFA yield of the strain C is 64.8, indicating that the strain A has obvious advantages; and an LTA yield of the strain B was 255.0, an LTA yield of the strain A was 210.4, and an LTA yield of the strain C was 178.0, indicating that, although the strain B has the highest LTA yield, the strain A also has obvious advantages.

Figure 2:
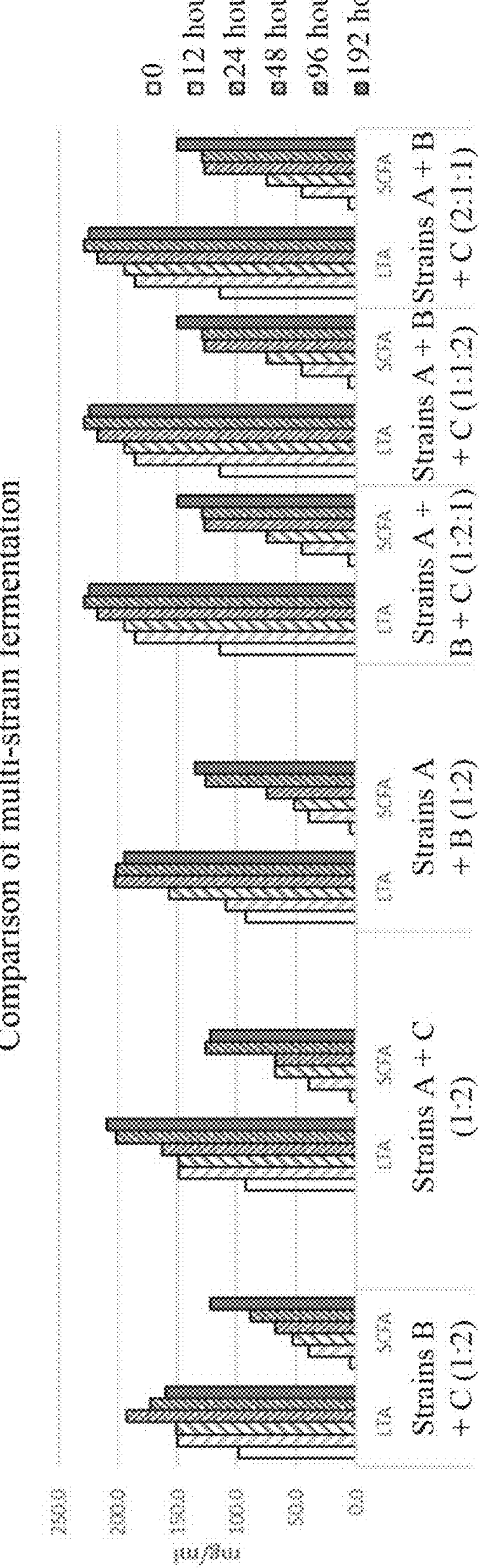
FIG. 2 shows fermentation effects of mixed bacteria of various bacterial strains in different ratios.

In terms of active substance yields after fermentation with mixed bacteria, fermentation effects after fermentation with mixed bacteria in different ratios are shown in FIG. 2. With reference to comparison among the inoculation proportions in FIG. 1, it can be seen that a fermentation effect is significantly improved when different strains are used in a ratio of 1:1.

(B) Impact of a Fermentation Time on a Fermentation Effect of Mixed Bacteria

Since it was determined that the fermentation with the three strains had the optimal fermentation effect, in order to further determine an impact of a fermentation time, with reference to the above operations, a fermentation time in step (3) was adjusted (the three strains were mixed in a ratio of 1:1:1) to investigate an impact of a fermentation time on a fermentation effect. Specific results were shown in Table 3 below.

TABLE 3

Impacts of different fermentation times of multi-strain fermentation on LTA and SCFA contents in a fermentation broth

| Fermentation time, h | 0 | 12 | 24 | 48 | 96 | 192 |
|---|---|---|---|---|---|---|
| LTA content (pg/mL) | 122.5 | 183.6↑ | 258.9↑ | 318.4↑ | 318.8 | 318.6 |
| | Improvement rate, % | 49.88 | 41.01 | 22.98 | 0.13↓ | −0.06↓ |
| SCFA content (μg/mL) | 0 | 68.9↑ | 89.6↑ | 116.4↑ | 116.8 | 116.9 |
| | Improvement rate, % | — | 30.04 | 29.91 | 0.34↓ | 0.09↓ |

Note:
"↑" or "↓" in the table indicates an increase or a decrease.

The improvement rate is calculated as follows:

$$R = \frac{C_n - C_0}{C_0} \times 100\%,$$

where $C_0$ represents a concentration (μg/mL) of LTA or SCFA detected at a stage before fermentation, $C_n$ represents a concentration (μg/mL) of LTA or SCFA detected at a stage after continuous fermentation, and R represents an improvement rate (%).

It can be seen from Table 3 that the LTA and SCFA contents gradually increase with the extension of a fermentation time, but are basically stable after 48 h of fermentation, indicating that 48 h is the optimal fermentation time; and an actual fermentation time can be 45 h to 50 h.

(C) Impact of a Material Ratio on a Fermentation Effect

Since the optimal fermentation bacterial solution ratio and the optimal fermentation time were determined in steps (A) and (B), respectively, in order to further investigate an impact of a material ratio on a fermentation effect, with reference to the above operations, a material ratio in step (1) was adjusted (the fermentation time in step (2) was 48 h, and the three strains were mixed according to a ratio of 1:1:1) to investigate an impact of a material ratio on a fermentation effect. Specific results were shown in Table 4 below.

TABLE 4

Impacts of different process water-to-wheat bran ratios on LTA and SCFA contents in a fermentation broth (fermentation time: 48 h)

| Process water-to-wheat bran ratio | 1:1 | 3:1 | 5:1 | 8:1 | 10:1 | 15:1 |
|---|---|---|---|---|---|---|
| LTA content (pg/mL) | 122.6 | 130.5↑ | 194.4↑ | 318.6↑ | 354.9↑ | 303.9↓ |
| | Improvement rate, % | 6.44 | 48.97 | 63.89 | 11.39↓ | −14.37↓ |
| SCFA content (μg/mL) | 0 | 68.1↑ | 88.5↑ | 115.1↑ | 115.4 | 115.5 |
| | Improvement rate, % | — | 29.96 | 30.06 | 0.26↓ | 0.09↓ |

It can be seen from Table 4 that the LTA and SCFA contents gradually increase with the increase of the process water-to-wheat bran ratio, but decrease slightly when the process water-to-wheat bran ratio exceeds 15:1, and thus the optimal process water-to-wheat bran ratio is 8:1 to 10:1.

(D) Impact of an Inoculum Size on a Fermentation Effect

Since an inoculum size during fermentation also often bad a specified impact on a fermentation effect, with reference to the above operations, the inventors adjusted an inoculum size in step (2) (a material ratio in step (1) was 8:1 and a fermentation time in step (2) was 48 h) to investigate an impact of an inoculum size on a fermentation effect. Specific results were shown in Table 5 below.

TABLE 5

Impacts of different inoculum sizes on LTA and SCFA contents in a fermentation broth (fermentation time: 48 h)

| | Inoculum size, % | 1 | 5 | 10 | 15 | 20 | 25 |
|---|---|---|---|---|---|---|---|
| LTA | Content (pg/mL) | 122.6 | 130.5↑ | 318.6↑ | 346.1↑ | 415.3↑ | 498.4↑ |
| | Improvement rate, % | — | 6.44 | 144.14 | 8.63 | 19.99 | 20.01 |
| SCFA | Content (μg/mL) | 0 | 70.1↑ | 91.1↑ | 118.5↑ | 128.8↑ | 141.9↑ |
| | Improvement rate, % | — | — | 29.96 | 30.08 | 8.69↓ | 10.17↓ |

It can be seen from Table 5 that the LTA content gradually increases with the increase of the inoculum size, but the SCFA content is basically stable after the inoculum size exceeds 20%, and thus the optimal inoculum size is 10% to 15%.

INDUSTRIAL APPLICABILITY

With the present disclosure, nutrients in wheat starch wastewater and wheat bran can be deeply extracted to prepare a postbiotic solution including high contents of LTA and SCFA without additionally supplementing nutrients. The present disclosure is conducive to reducing a wastewater treatment cost of a related enterprise and protecting the environment, can turn waste into treasure and increase an added value of an agricultural product, and can also lay a specified technical foundation for extending an industrial chain of wheat deep-processing and improving an industrial value of deep processing technology.

Finally, it should be noted that the above embodiments are merely intended to illustrate the technical solutions of the present disclosure, rather than to limit the present disclosure. Those of ordinary skill in the art may make other modifications or equivalent replacements to the technical solutions of the present disclosure without departing from the spirit and scope of the technical solutions of the present disclosure, but such modifications or equivalent replacements should fall within the scope defined by the claims of the present disclosure.

What is claimed is:

1. A fermentation process for preparing a postbiotic solution comprising the following steps:

(1) preparing a fermentation matrix by mixing wheat starch wastewater and wheat bran in a mass ratio of 1:1 to 12:1 of the wheat starch wastewater to the wheat bran to obtain a resulting mixture, sterilizing the resulting mixture by heating to obtain a sterilized mixture, and cooling the sterilized mixture to room temperature to obtain a fermentation matrix;

(2) inoculating fermentation strains by:

(a) culturing *Paenibacillus polymyxa* (*P. polymyxa*), (b) culturing *Brachybacterium paraconglomeratum* (*B. paraconglomeratum*), and (c) culturing *Flavobacterium pectinovorum* (*F. pectinovorum*), mixing each resulting culture of (a)-(c) to obtain a mixed fermentation broth, inoculating the mixed fermentation broth into the fermentation matrix obtained in step (1) under sterile conditions, and conducting fermentation at 25° C. to 37° C. for 48 hours to 192 hours to produce a fermentation system; and (3) isolating and extracting the postbiotic solution by filtering the fermentation system obtained in step (2) to obtain a resulting filtrate, subjecting the resulting filtrate to primary centrifugation to obtain a first supernatant, collecting the first supernatant, and subjecting the first supernatant to secondary centrifugation to obtain a second supernatant; wherein the second supernatant is the postbiotic solution and wherein the postbiotic solution comprises a lipoteichoic acid (LTA) and a short-chain fatty acid (SCFA).

2. The fermentation process according to claim 1, wherein in step (1), the wheat starch wastewater and the wheat bran are mixed in a mass ratio of 8:1 to 10:1 of the wheat starch wastewater to the wheat bran.

3. The fermentation process according to claim 1, wherein in step (2):

*P. polymyxa* is *P. polymyxa* with an accession No. of CGMCC 1.15984,

*B. paraconglomeratum* is *B. paraconglomeratum* with an accession No. of CGMCC 1.838, and

*F. pectinovorum* is *F. pectinovorum* with an accession No. of CGMCC 1.12362.

4. The fermentation process according to claim 1, wherein in step (2):

the number of viable bacteria in each resulting culture of (a)-(c) is not less than $1\times10^6$ bacteria/mL and wherein mixing each resulting culture of (a)-(c) comprises mixing each of (a)-(c) at a volume ratio of 1:1:1.

5. The fermentation process according to claim 1, wherein in step (3), the primary centrifugation is conducted at 1,000 r/min for 30 min and the secondary centrifugation is conducted at 5,000 r/min for 30 min.

* * * * *